US006410782B1

(12) United States Patent
VanGulik et al.

(10) Patent No.: US 6,410,782 B1
(45) Date of Patent: Jun. 25, 2002

(54) DIPHOSPHONIC ACID SALTS FOR THE TREATMENT OF OSTEOPOROSIS

(75) Inventors: Fred VanGulik, Laan Copes van Cattenburch (NL); Antonio Parente, Sant Just Desvern (ES)

(73) Assignees: Geange Ltd., Dublin (IE); Eurodrug Ltd., Hong Kong (CN); Lipotec SA, De Llobregat (ES)

( * ) Notice: Subject to any disclaimer, the term of this patent is extended or adjusted under 35 U.S.C. 154(b) by 0 days.

(21) Appl. No.: 09/446,617

(22) PCT Filed: Jul. 8, 1997

(86) PCT No.: PCT/EP98/04238

§ 371 (c)(1),
(2), (4) Date: Apr. 3, 2000

(87) PCT Pub. No.: WO99/02539

PCT Pub. Date: Jan. 21, 1999

(30) Foreign Application Priority Data

Jul. 9, 1997 (IT) .......................... MI97A1628

(51) Int. Cl.[7] .................................. C07F 9/38
(52) U.S. Cl. ........................ 562/13; 562/8; 562/23; 562/25
(58) Field of Search ............... 562/8, 11, 13, 562/16, 23, 25

(56) References Cited

U.S. PATENT DOCUMENTS

| 4,624,947 A | * | 11/1986 | Blum et al. |
| 4,814,326 A | * | 3/1989 | Rosini et al. |
| 4,830,779 A |   | 5/1989 | Seiji Maeno |
| 5,389,261 A | * | 2/1995 | Daly et al. |
| 5,624,917 A | * | 4/1997 | Kitano et al. |

FOREIGN PATENT DOCUMENTS

| DD | 150744  | 9/1981  |
| DD | 273650  | 11/1989 |
| EP | 781804  | 7/1997  |
| EP | 292190  | 11/1998 |
| FR | 2142051 | 1/1973  |
| GB | 1508772 | 4/1978  |
| GB | 2118042 | 10/1983 |
| WO | 9200721 | 1/1992  |

OTHER PUBLICATIONS

CA:127:136497 abs of EP 781804, Jul. 1997.*
CA:109:232705 abs of JP63135581, Jun. 1988.*
CA:126:281009 abs of JP09053193, Feb. 1997.*
CA:125:320562 abs of WO9631124, Oct. 1996.*
CA:103:215563 abs of DD222600, May 1985.*
Chemical Abstracts, vol. 121, No. 11, Sep. 12, 1994 Abstract No. 125254, Yoneshima N et al: "1,3,5(10)–estratriene–3, 17.beta.–diol 17–(3,3–diphosphono) propionate for prevention and treatment of osteoporosis" XP002081479 see abstract.
Chemical Abstracts, vol. 126, No. 21, May 26, 1997 Abstract No. 281009, Sao T et al: "Scale dissolving aqueous solutions containing alkanolamine salts" XP002081480 see abstract.

* cited by examiner

Primary Examiner—Jean F. Vollano

(57) ABSTRACT

Diphosphonates or their salts between acids and linear, branch substituted and non-substituted, cyclic, heterocyclic and aromatic amino alcohols are used to treat osteoporosis. Pharmaceutical compositions and therapeutic methods of treating osteoporosis are described.

4 Claims, No Drawings

DIPHOSPHONIC ACID SALTS FOR THE TREATMENT OF OSTEOPOROSIS

This application is a national phase entry under 35 U.S.C. § 371 of PCT/EP98/04238, filed Jul. 8, 1998.

OBJECT OF THE PRESENT INVENTION

Object of the present invention are salts of diphosphonic acids or diphosphonates and a procedure for their preparation.

Object of the present invention is also the use of mentioned salts of diphosphonic acids or diphosphonates for treatment of osteoporosis.

Object of the present invention are again pharmaceutical compositions which contain, as active principle, the mentioned salts of diphosphonic acids or diphosphonates and the use of these compositions in the treatment of osteoporosis.

STATUS OF THE TECHNIQUE

As well known osteoporosis is a disease of the skeleton that is characterised by the disarrangement and by the loss of bone tissue, with increase of skeleton fragility and predisposition to fractures.

As an example, is reported that in US this disease afflicts more than 25 millions of persons and it causes 1.300.000 fractures every year.

The social cost is consequently very high accounting for more than 10 billions of US dollars per year. The same figures are reported in Europe and in Japan.

The elderly is the population with the highest risk. Unfortunately the problem is becoming progressively more serious in the view of the progressive grow old of population. A forecast of the fracture incidence in the future sixty years assumes an increase of at least three times. Women are more exposed that men, particularly during the first 5 years after the menopausal period.

At present, from a therapeutic viewpoint, either a monotherapy with fluorides, as reported by Melmon & Morrelli, Clinical Pharmacology: Basic Principles in Therapeutics, 497 (1992), N. Engl. J. Med. 306,446 (1982) is used, or addition use of combined therapies with calcium, fluoride and oestrogens are reported to retain some advantages as compared to the mono-therapy.

Alternatively, another class of compounds prescribed for the treatment of osteoporosis includes disphosphonates; these agents are mostly administered by oral route, but besides having the unsolved inconvenient of a poor absorption (from 1 to 5% of dose), they also develop, as primary adverse events, oesophagitis and gastro-intestinal disorders of moderate-severe intensity.

To overcame this inconvenient, several clinical studies have been carried out, in the search of new compounds that combine a high pharmacological activity together with a better tolerability an increased bioavailability as compared to known available compounds.

For example, in the treatment of uro-litiasis and for inhibition of bone resorption, diphosphonic acids and their salts are described in the U.S. Pat. No. 4,621,077; namely, the biological activities of mentioned phosphonic acids or their corresponding sodium salts are reported. The degree of absorption, i.e. the bioavailability, of those compounds resulted however very low and for this reason, in order to achieve in the body active concentrations of the active principle, high doses had to be administered with consequent occurrence of gastro-intestinal adverse reactions which worse tolerability.

OBJECTIVES OF THE INVENTION objective of the present invention is to make available diphosphonates that have an increased bioavailability when administered by oral route.

Objective of the present invention is also to make available diphosphonates that are more effective in the treatment of osteoporosis while retaining a lower incidence of oesophagus and gastro-intestinal adverse events as compared to those known compounds already available.

Again, objective of the present invention is to make available diphosphonates which can be administered both by oral or intravenous route.

Again, objective of the present invention is to make available diphosphonates that display an improved therapeutic index in treatment of osteoporosis as compared to the known drugs at present used in the medical practice.

Objective of the present intention is also to make available a procedure for the preparation of diphosphonates.

Objective of the present invention is also to make available pharmaceutical formulations, containing at least one diphosphonate as active principle, easy to be administered, well tolerated and able to allow a high therapeutic index.

DESCRIPTION OF THE INVENTION

These and other objectives with further advantages which are clarified in the description below, are obtained by diphosphonates or salts of diphosphonic acids and linear, branched, substituted and non-substituted, cyclic, heterocyclic, aromatic amino-alcohol derivatives, said diphosphonates having the following general formula:

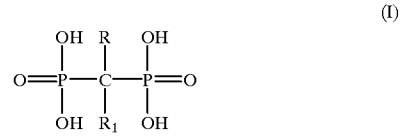

(I)

where $R=R_1$ or $R \neq R_1$ and R and $R_1$ are chosen among H, OH, Cl, linear or branched, substituted or not substituted alkyl groups, linear or branched, substituted or not substituted alkylidenic chain, or they are chosen among:

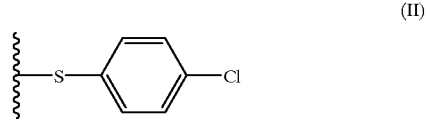

(II)

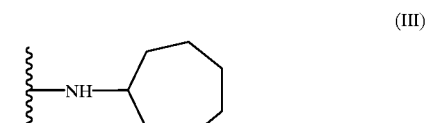

(III)

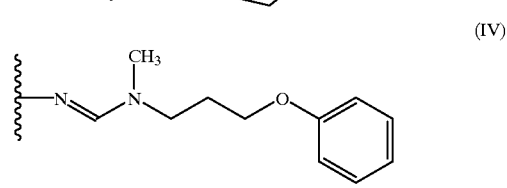

(IV)

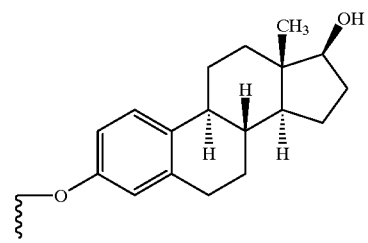 (V)

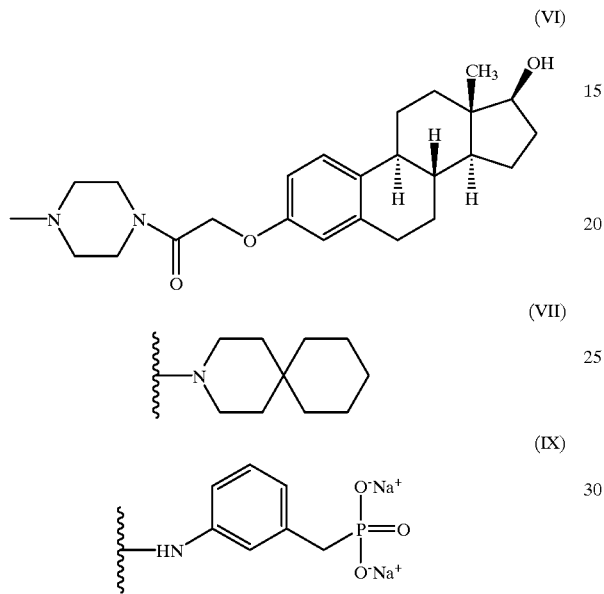 (VI)

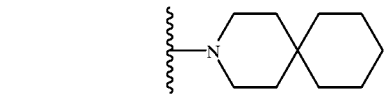 (IX)

More particularly, according to the present invention, mentioned amino-alcohols are chosen among linear and branched amino-alcohols, and specifically they are chosen among:

H₂N—CH₂CH₂OH (XVI)

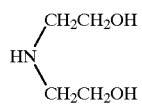 (XVII)

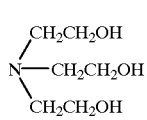 (XVIII)

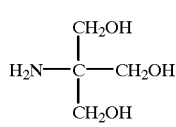 (XIX)

(CH₃)₃N⁺—CH₂CH₂OH (XX)

Always according to the present invention, mentioned amino-alcohols are cyclic and hetero cyclic amino-alcohols and are chosen among

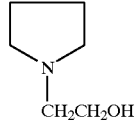 (XXI)

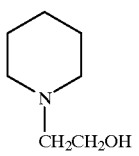 (XXII)

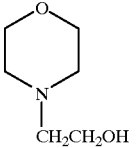 (XXIII)

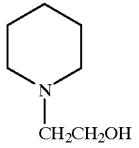 (XXIV)

Again, according to the present invention, mentioned substituted alkylidenic chain, defined in formula (I), is chosen equal to:

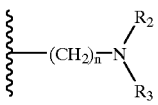 (X)

with n within 1 and 6, where $R_2=R_3$ or $R_2 \neq R_3$ and $R_2$ and $R_3$ are chosen among H, linear or branched, cyclic, substituted or non-substituted alkyl groups, or $R_2$ and $R_3$ represent, together with the nitrogen atom N, an aliphatic or aromatic hetero-cycle.

Always according to the present invention, the substituted alkylidenic chain, defined in formula (I), is also chosen equal to

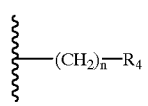 (XI)

where n is within 1 and 6 and $R_4$ is chosen among:

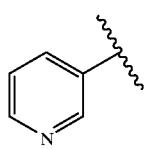 (XII)

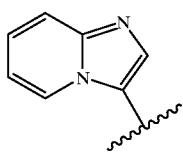
(XIII)

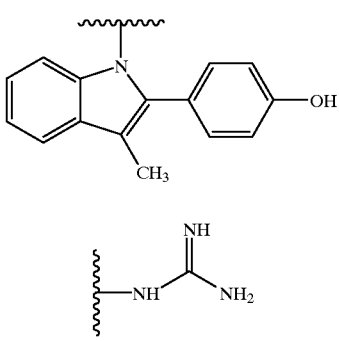
(XIV)

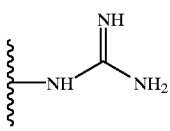
(XV)

According to the present invention, of particular interest appeared the salt obtained between a diphosphonic acid of general formula (I), where R≠R$_1$, R is chosen equal to OH and R$_1$ is chosen as substituted linear alkylidenic chain of formula (X), where n=3, R$_2$ and R$_3$ are equal to H according to the following formula:

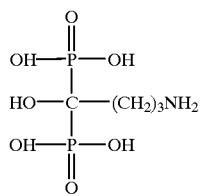
(XXVI)

or 4-amino-1-hydroxybutane-1,1-biphosphonic acid (alendronic acid) and one branched amino-alcohol of formula

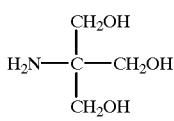
(XIX)

or 2-amino-2-hydroxymethyl-1,3-propanediol (trometamine). Mentioned salts, always according to the present invention, depending upon the preparation procedure, are formed by the residues corresponding to the diphosphonic acid and the amino-alcohol in a variable molar ratio, while they can be advantageously used in the treatment of osteoporosis. Mentioned molar ratios can vary between 1:1 and 1:2 (diphosphonic acid : amino-alcohol).

Diphosphonates according to the prior art, retain a non satisfactory pharmacokinetic profile, characterised by a very poor absorption from the gastro-intestinal tract, with a systemic bioavailability ranging between 1 to 5% of the oral dose. About 50% of the absorbed dose is then eliminated with the urine in 24 hours, while the dose left is retained by bone tissue and afterwards eliminated very slowly. The unabsorbed diphosphonate is instead eliminated with the faeces.

This behaviour has to be attributed to the physico-chemical properties of the products, which being highly hydro-soluble hardly penetrate the lipid membranes. Oral doses much higher than those bioavailable are then necessary to achieve and maintain a therapeutic effective concentration at the target site (bone), with consequent increase of the local gastro-intestinal adverse events like nausea and diarrhoea.

Diphosphonates according to the present invention, due to the lower dissociation degree of the salt and to the physico-chemical properties of the amino-alcohol, are characterised by a lower water solubility and an increased lipid solubility as compared to the known diphosphonates (sodium salts).

These characteristics confer remarkable advantages in the absorption process trough the biological membranes, thus improving bioavailability.

In addition, diphosphonates of the present invention, did show a promising pharmaco-toxicological profile in relation to the expected use in the therapy of osteoporosis.

The diphosphonates of the present invention show a good efficacy in stimulating bone growth, this being probably due to the known property of amino-alcohols of subtracting toxic-radicals produced by reactive species.

The diphosphonates of the present invention can be easily administered both by intravenous and oral route. In this latter case, the use of pharmaceutical systems able to control the release of the active principle, are particularly advantageous. These systems include liposomes, niosomes and similar matrices, possibly added appropriate carriers which are of easy use and allow a sustained release of the active principle.

The diphosphonates of the present invention are advantageously prepared by reacting a solution or suspension of diphosphonic acid of general formula (I) with an amino-alcohol dissolved in a proper solvent; the reaction product (salt) between the diphosphonic acid and the amino-alcohol, obtained by cooling the resulting solution, is then purified according to known techniques.

As a non-limitative example of the present invention, some examples referring to the preparation of the salt obtained by reacting the diphosphonic acid of formula:

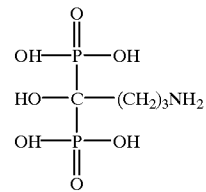
(XXVI)

and the amino-alcohol of formula:

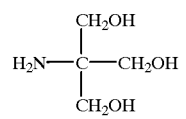
(XIX)

are hereafter described.

EXAMPLE 1

4-amino-1-hydroxybutane-1,1-biphosphonic acid, (alendronic acid, 1g, 4.016 mmoles),was dissolved into 20 mL of CH$_2$Cl$_2$/methyl alcohol (9:1). 2-amino-2- hydroxymethyl-1,3 propandiol, (trometamine, 486 mg, 4.016 mmoles) dissolved in 5 mL of $CH_2Cl_2$/methyl alcohol (9:1) was added under stirring to the alendronic acid solution. The white precipitate formed, was filtered and dried under vacuum.

1.263 g of alendronate trometamine salt were obtained, yield 85%.

EXAMPLE 2

4-amino-1-hydroxybutane-1,1-biphosphonic acid, (alendronic acid, 1g, 4.016 mmoles), was suspended into 20 mL water. 2-amino-2-hydroxymethyl-1,3 propandiol, (trometamine, 486 mg, 4.016 mmoles) was added, under stirring, to the aqueous solution of alendronic acid. Solids rapidly dissolved in water, the suspension becames clear, while the resulting solution, having a pH=4.18, wass frozen and lyophilised to give a white powder. 1.480 g of alendronate trometamine salt were obtained, yield 99%.

EXAMPLE 3

4-amino-1-hydroxybutane-1,1-biphosphonic acid, (alendronic acid, 1 g, 4.016 mmoles),was suspended into 40 mL water. 2-amino-2-hydroxymethyl-1,3 propandiol, (trometamine, 972 mg, 8.032 mmoles) was added, under stirring, to the aqueous solution of alendronic acid. Solids rapidly dissolved in water, the suspension becomes clear, while the resulting solution had a pH=7.14 was frozen and lyophilised to give a white powder.

1.97 g of alendronate trometamine salt were obtained, yield 99%.

EXAMPLE 4

4-amino-1-hydroxybutane-1,1-biphosphonic acid, (alendronic acid, 1 g, 4.016 mmoles),was suspended into 5 mL water. 2-amino-2-hydroxymethyl-1,3 propandiol, trometamine (486 mg, 4.016 mmoles) was added, under stirring, to the aqueous solution of alendronic acid. Solids rapidly dissolved in water, the suspension becames clear, while the resulting solution had a pH=4.18. !0 mL of iso-propylic alcohol were added and the resulting solution was cooled at a temperature of −10° C. overnight. The precipitate formed was filtered, washed twice with cool iso-propylic alcohol, then was dried under vacuum.

743 mg of alendronate trometamine salt were obtained, yield 50%.

The product obtained according to the procedures reported in the examples 1,2 and 4, was analysed by IR and $^1$H-NMR spectroscopy.

The melting point was 180.53° C. $^1$H-NMR (300 MHz), ($D_2O$) δ=3.615 (s 6H, $CH_2O$) ; 2.920 (t, 2H, $N^+$—$CH_2$, J=6.5 Hz); 1.900 (m, 2H, $NCH_2$ $C\underline{H}_2$ $CH_2$); 1.890 (t, 2H, $NCH_2$ $CH_2$ $C\underline{H}_2$, J=6.5 Hz).

As an example, a non-limitative example is hereafter reported, referring to the preparation of a pharmaceutical formulation of the salt obtained by reacting the diphosphonic acid of formula

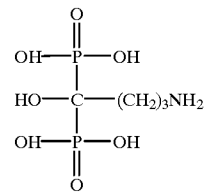

(XXVI)

and the amino-alcohol of formula

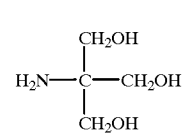

(XIX)

EXAMPLE 5

Alendronate Trometamine Salt Formulated in Liposome Matrix.

LECINOL LS (liposomes) , 20%
SALT OF 4-AMINO-1-HYDROXYBUTANE-1,1-BIPHOSPHONIC ACID, (ALENDRONIC ACID) AND 2-AMINO-2-HYDROXYMETHYL-1,3 PROPANDIOL, (TROMETAMINE) , 15%
(Ratio between alendronic acid and trometamine ≅1:1)
TROMETAMINE BASE; 1%
CHOLESTEROL; 4%
PROPYLENGLYCOL; 10%
ETHANOL: 1%
CARBOPOL ETD 2020; 0,5%
Na $_2$EDTA; 0.15%
NIPAGIN; 0.2%
PHENONIP (CONSERVATIVE); 0,3%
CITRIC ACID; 0.2
BHT; 0.01
WATER; to 100%

Dealing with the evaluation of the pharmaco-toxicological activity of the salts obtained by reacting diphosphonic acids of general formula (I) and amino-alcohols according to the present invention, biological tests were carried out taking as test compound the product alendronate trometamine obtained as described in the examples above.

EFFICACY

A study on a tissue culture (scalp slices of new-born mouse prepared according to the method described by A. Togari, Gen. Pharmacol. 24, 1133, 1993) was performed. At the end of the culture period, the tissue added μmolar concentrations of the title product, was homogenised in saline plus 0.1% Triton X-100.

The obtained homogenate was used to determine alkaline phosphatase (as osteoblastic activity index) and N-acetylglycosaminidase (as osteoclastic activity index). The test product starting from the 10 μmolar concentration, was shown to be able to activate in a significant manner the osteoblastic activity (alkaline phosphatase) and to inhibit the osteoclastic activity (N-acetylglycosaminidase).

TOXICITY

The compound when administered orally to mice at the dose of 50 mg/kg, which is a multiple (x300 times) of the human therapeutic dose, did not cause the onset of apparent toxic symptoms.

BIOAVAILABILITY

A study carried out in rats administered both orally and intravenously the test compound, alendronate trometamine, at the 10 mg/kg dose allowed calculation of a mean absolute bioavailability equal to 8%. Calculation was performed on 0–24 hours urine elimination of alendronic acid according to the method described in J. of Chromatography, 533, 183–193, 1992: "Improved determination of the biphosphonate alendronate in human plasma and urine by automated pre-column derivatisation and HPLC with fluorescent and electro-chemical detection".

What is claimed is:

1. A pharmaceutical composition for the treatment of osteoporosis comprising, together with a carrier or a diluent, a salt of a diphosphonic acid of formula

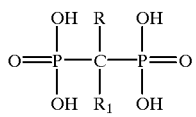

(I)

where $R=R_1$ or $R \neq R_1$ and R and $R_1$ are selected from:

H, OH, Cl, linear or branched, substituted or not substituted alkyl groups, a group of formula (X)

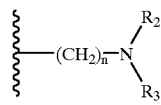

(X)

where n is 1 to 6 and $R_2=R_3$ or $R_2 \neq R_3$ and $R_2$ and $R_3$ are selected from H and linear or branched, cyclic, substituted or unsubstituted alkyl groups, a group of formula (II), (III), (IV) or (IX):

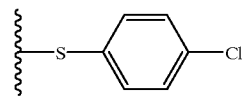

(II)

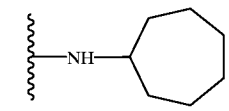

(III)

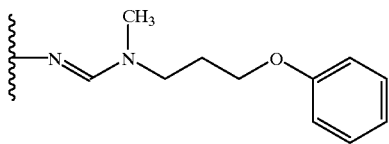

(IV)

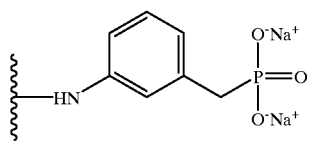

(IX)

and an amino-alcohol of formula (XVI) to (XIX):

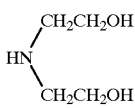

(XVII)

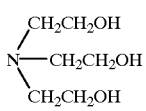

(XVIII)

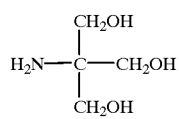

(XIX)

provided that when $R \neq R_1$ and R=OH, $R_1=CH_3$ the amino-alcohol is not tromethamine (XIX), triethanolamine (XVIII), diethanolamine (XVII) or ethanolamine (XVI);

when $R \neq R_1$ and R=H, $R_1=CH_2OH$ the amino-alcohol is not ethanolamine (XVI); and further provided that when R=OH and $R_1=C_{11}H_{23}$ or $C_{17}H_{35}$ the amino—alcohol is not triethanolamine (XVIII).

2. The pharmaceutical composition according to claim 1 wherein the salt is 4-amino-1-hydroxybutane-1,1-diphosphonic acid (alendronic acid) and tromethamine (XIX).

3. The pharmaceutical composition according to claim 1 for parenteral administration.

4. The pharmaceutical composition according to claim 1 which is contained in liposomes or niosomes.

* * * * *